United States Patent
Terry

(10) Patent No.: US 7,955,636 B2
(45) Date of Patent: Jun. 7, 2011

(54) ANTIMICROBIAL COATING

(75) Inventor: Richard Terry, Conyers, GA (US)

(73) Assignee: C.R. Bard, Inc., Murray Hill, NJ (US)

( * ) Notice: Subject to any disclaimer, the term of this patent is extended or adjusted under 35 U.S.C. 154(b) by 172 days.

(21) Appl. No.: 12/281,537

(22) PCT Filed: Mar. 2, 2007

(86) PCT No.: PCT/US2007/063180
§ 371 (c)(1),
(2), (4) Date: Feb. 18, 2009

(87) PCT Pub. No.: WO2007/130734
PCT Pub. Date: Nov. 15, 2007

(65) Prior Publication Data
US 2009/0319035 A1    Dec. 24, 2009

Related U.S. Application Data

(60) Provisional application No. 60/778,758, filed on Mar. 3, 2006.

(51) Int. Cl.
*A61L 33/00* (2006.01)
(52) U.S. Cl. ............... 427/2.1; 427/2.12; 427/421.1
(58) Field of Classification Search ............ 427/2.1
See application file for complete search history.

(56) References Cited

U.S. PATENT DOCUMENTS

| 5,077,352 A | 12/1991 | Elton |
| 5,160,790 A | 11/1992 | Elton |
| 5,179,174 A | 1/1993 | Elton |
| 5,290,585 A | 3/1994 | Elton |
| 5,447,966 A | 9/1995 | Hermes et al. |
| 6,329,488 B1 | 12/2001 | Terry et al. |
| 6,596,401 B1 | 7/2003 | Terry et al. |
| 6,716,895 B1 | 4/2004 | Terry |
| 7,378,156 B2 | 5/2008 | Terry |
| 2003/0203991 A1 * | 10/2003 | Schottman et al. ......... 523/334 |
| 2008/0199536 A1 | 8/2008 | Terry |
| 2008/0199623 A1 | 8/2008 | Terry |

FOREIGN PATENT DOCUMENTS

WO    WO2004001773    *    3/2004

OTHER PUBLICATIONS

International Search Report for PCT/US07/63180, dated Dec. 13, 2007.

* cited by examiner

*Primary Examiner* — Michael Barr
*Assistant Examiner* — Andrew Bowman
(74) *Attorney, Agent, or Firm* — Greenblum & Bernstein, PLC

(57) ABSTRACT

Described herein are coatings containing water-soluble oligodynamic metal salts that are formulated and applied from hydrophobic solvents. In particular, articles of manufacture comprising polymer coatings containing oligodynamic metal salts can include hydrophobic polymer coatings made from water-reactive monomers and hydrophilic polymers compounded in hydrophobic solvents which contain a small amount of water that aids in the solubilization and suspension of the oligodynamic metal salts. Methods of preparing these antimicrobial polymer coatings, and methods of coating a substrate to produce an article of manufacture having an antimicrobial polymer coating are also described.

10 Claims, No Drawings

ANTIMICROBIAL COATING

The present application claims priority to U.S. Provisional Application No. 60/778,758, filed Mar. 3, 2006, the disclosure of which is incorporated herein by reference in its entirety.

Some metals, including silver and silver salts, are used in the medical field as antimicrobial agents. For example, silver in the form of metal, salts, colloids, and complexes has been used to prevent and to control infection relating to the use of medical devices. Silver has been deposited directly on device surfaces, distributed within device materials or formulated into coatings and deposited onto devices. Many other metals, including gold, zinc, copper, and platinum, have also been found to possess antimicrobial properties, both alone and in combination with silver. These and other metals have been shown to provide antimicrobial behavior even in minute quantities, a property referred to as "oligodynamic."

Oligodynamic metals have been used with medical devices, such as catheters, cannulae and stents, to reduce or prevent bacterial growth These metals may be included as a part of the material forming the device, deposited on the surface of the device, or they may be included in coatings. For example, U.S. Pat. No. 6,716,895 to Terry describes medical device coatings including colloids of oligodynamic metals for use as antimicrobial coatings U.S. Pat. No. 6,716,895 is herein incorporated by reference in its entirety. Oligodynamic metals may be incorporated into polymer compositions by many different methods. The coatings may also include materials having other beneficial properties. For example, the coatings may be lubricious and hydrophilic, making them slippery when in contact with water or body fluids. Thus, oligodynamic metals may be included as part of a coating for a polymeric medical device.

Unfortunately, for many coating formulations that contain water reactive components and/or are formulated in hydrophobic organic solvents, it is difficult to introduce oligodynamic metal salts because they ale typically only soluble in water or sometimes alcohol. In such hydrophobic coatings, oligodynamic metal salts are poorly soluble and effective concentrations ate difficult to achieve in the coating solution. Because of this limitation, prior methods of incorporating oligodynamic metals in hydrophobic coating solutions have relied upon suspension or dispersion of insoluble materials within the coating solution. For example, coatings containing components having isocyanate functional groups that cure through the polymerization of these isocyanate groups with other functional groups, such as hydroxyl or amine groups, will also react with water or alcohol. Such side reactions reduce the degree of polymerization and crosslinking in the coating, lowering the overall molecular weight of the polymer in the coating. This can lead to degradation of coating properties and cause problems with coating adhesion to the substrate or coating strength and durability. Because of the potential for side reactions with water, such coatings are typically compounded in anhydrous and/or highly hydrophobic solvent systems to limit the amount of water in the coating formulation that could cause side reactions with reactive monomers/polymers and interfere with adhesion or formation of the coating.

This problem is particularly apparent with hard-to-coat substrates, such as silicones. For example, U.S. Pat. No. 6,329,488 to Terry et al. (herein incorporated by reference in its entirety), describes silane copolymers useful in coating hard-to-coat substrates, such as silicone. These silane copolymers may be formed by the reaction of one or more polyisocyanates with one or more lubricious polymers having functional groups that are reactive with an isocyanate functional group and with one or more organo-functional silanes having at least two functional groups that ate reactive with an isocyanate functional group and at least one functional group reactive with a silicone rubber substrate. These coatings may be formulated as a single coating or as a primer coating that is over-coated with another coating. Even when the primer coating is formulated so that it can tolerate the addition of water or alcohol (and therefore the addition of salts of oligodynamic metals dissolved in water or alcohol), it was found by the inventor that the total concentration of oligodynamic metal (e.g., silver) achieved when coating a silicone Foley catheter typically could not exceed 4 to 5 $\mu g/cm^2$ of the surface coated. By comparison, corresponding silver loading for latex Foley catheter with a comparable antimicrobial coating (as described in U.S. Pat. No. 6,716,895 to Terry) was approximately 14 $\mu g/cm^2$, but could be as high as 50 $\mu g/cm^2$.

Thus, there is a need for coatings that allow increased levels of oligodynamic metals (particularly water-soluble oligodynamic metals) in coatings that are sensitive to water and/or alcohol, and methods of formulating and applying such coatings. The coatings and methods described herein address some of the problems identified above.

Accordingly, described herein are antimicrobial coatings containing water-soluble oligodynamic metals, methods of formulating and applying them to achieve relatively high levels of the water-soluble oligodynamic metals in coatings, even when the coating formulation contains components which are reactive with water or alcohol and are compounded in hydrophobic solvents. In particular, antimicrobial and lubricious polymeric coatings and articles of manufacture comprising such coatings are described, as well as methods of making and methods of applying such coatings.

Articles of manufacture comprising polymer coatings containing oligodynamic metal salts can include hydrophilic polymer coatings made from water-reactive isocyanate-containing monomers and hydrophilic polymers compounded in hydrophobic solvents which contain a small amount of water that aids in the solubilization and suspension of the oligodynamic salts. The article of manufacture may have a surface substrate comprising a polysiloxane rubber (e.g., silicone). In some variations, a primer layer (e.g., a silane copolymer primer coating) is applied to the substrate, and the coating of the invention is applied on top of the primer layer. The water-soluble oligodynamic metal salt may be, for example, a silver salt such as silver nitrate or silver acetate.

Remarkably, even though the coatings of the invention are compounded in highly hydrophobic solvents to reduce the likelihood of reaction of the water-reactive functional groups with water in the coating solution, water-soluble, oligodynamic metal salts may be included in the coatings of the invention when a small amount (100 to 1000 ppm) of water is added to the formulation. In some variations, the resulting coating has a surface concentration of oligodynamic metal salt greater than about 5 $\mu g/cm^2$, greater than about 10 $\mu g/cm^2$ or even greater than about 20 $\mu g/cm^2$. The metal salt may be released from the coating when the article is placed in a fluid (e.g., water or bodily fluid) environment. The release profile may span several days or several weeks.

In some variations, the article of manufacture comprises a medical device. For example, the article of manufacture may comprise a catheter, an endotracheal tube, a tracheostomy tube, a wound drainage device, a wound dressing, a stent, an implant, an intravenous catheter, a suture, a shunt, a glove, a condom, a contact lens, a gastrostomy tube, medical tubing, cardiovascular products, heart valves, pacemaker leads, a guidewire, or urine collection devices.

The coating may comprise a polyurethane that is formed from a mixture of polyisocyanate and polyol in a hydrophobic solvent into which the oligodynamic metal salt is added. In some variations, the oligodynamic metal salts are added to a coating that comprises a hydrophilic polymer such as polyethylene oxide (PEO), polyethylene glycol or polyvinyl pyrrolidone (PVP) in addition to the polyisocyanate and polyol in a hydrophobic solvent, as described in U.S. Pat. Nos. 5,179,174 and 5,290,585 to Elton, each of which is incorporated herein by reference.

Also described herein are articles of manufacture comprising an antimicrobial and lubricious polymer coating, wherein the polymer coating is formed from a mixture of a polyisocyanate, a polyol, and a polyethylene oxide in a highly hydrophobic solvent, and including one or more water-soluble oligodynamic metal salts and a small amount of water. As described above, the article may be a catheter.

Also described herein are methods for the manufacture of an article. The method may include the steps of applying a coating composition to a substrate by spraying the coating composition onto the substrate or by dipping the substrate into the coating composition, wherein the coating composition comprises polymers, monomers, or any combination thereof in a hydrophobic solvent, and a water-soluble oligodynamic metal salt, and then drying the coating, wherein the surface concentration of oligodynamic metal salt is greater than about 5 $\mu g/cm^2$. Additionally, the concentration of oligodynamic metal salts in the coating formulation can be increased advantageously by the addition of a small amount of water to the formulation.

A method for coating a substrate is described. The method includes compounding a coating solution (the coating solution typically includes an polyisocyanate, a polyol and a hydrophilic polymer such as polyethylene oxide in a hydrophobic solvent), adding water to the coating solution to achieve a concentration of about 100-1000 ppm, adding a water-soluble oligodynamic metal salt to the coating solution, mixing for a period of time to solubilize the oligodynamic metal salt, and coating a substrate with the coating solution. In some variations, the substrate is silicone (e g., a catheter or other medical device).

The step of compounding the coating solution may include dissolving a hydrophilic polymer such as PEO in methylene chloride along with a polyol and a small amount of water and mixing the solution until the PEO has been dissolved and the water absorbed. The coating solution may be agitated by any appropriate means and for any appropriate time, including stirring the coating solution for greater than 24 hours. After the solution is formed, the desired oligodynamic salt or combination of salts is added and the agitation is continued for a period of one to three days ox more to allow the oligodynamic metal salts to dissolve in the solution. The solution is then filtered to remove any undissolved metal salt. Filtration may be performed using any appropriate filter, including size-specific filters, such as 25, 50, 100, 150 or 200 micron filters. The polyisocyanate is added last just before the substrate is coated to reduce reactions with water, but may be optionally added to the formulation at any time. The substrate coated by the coating may be a clean surface or it may be first treated or primed (e.g., with a silane copolymer coating) to improve the adherence of the coating.

It should be understood that although a number of the embodiments described herein describe urinary catheters, embodiments of the present invention may be applied in combination with any appropriate medical device, including but not limited to catheters such as Foley catheters. Furthermore, this invention need not be limited to catheters, or even to medical devices. As one of ordinary skill in the art would appreciate, variations of the invention may be applied to any appropriate device in which lubricious, antimicrobial articles of manufacture would be desirable.

Coatings

Many difficult to coat substrates must be first primed with a coating having one or more reactive groups to facilitate the adhesion of the final coating to the substrate. In some variations, more than one reactive coating may be used. For example a priming coat may be applied before a final coating of the desired exposed surface (a "top coat") is applied. The primer is designed to improve the adhesion of the final coating to the substrate. Because of the chemically inert nature of many difficult to coat substrates (such as silicones), both the primer and top coat that are employed generally utilize some type of reactive chemistry.

One of the most common reactive functional groups used to cure reactive coatings is the isocyanate group. One of the problems in using coatings that cure by the polymerization of isocyanate groups is that these groups will also react with water and alcohol. Because of this, such coatings are typically compounded in anhydrous and/or highly hydrophobic solvents or solvent systems to limit the amount of water in the coating that could cause side reactions with the isocyanate-containing monomers/polymers. If water is not controlled in such coatings, the isocyanate groups can be consumed by reaction with water reducing the coating adhesion the substrate, or otherwise reducing the effectiveness of the coating.

The water/alcohol sensitivity of some coating solutions has been problematic for the inclusion of oligodynamic metals as part of these coatings. For example, U.S. Pat. No. 6,716,895 (incorporated by reference) describes the inclusion of oligodynamic metals into reactive coatings. However, because the salts used to produce oligodynamic metal colloids (e.g., silver colloids) must be dissolved in water or alcohol, the inclusion of such oligodynamic metal colloids may interfere with the reactive coating chemistry, or the concentration of oligodynamic metal colloids in the coating may be limited by the need to reduce the amount of water or alcohol in the formulation. In general, the methods described herein may be used to incorporate oligodynamic metal salts into coatings formulated in highly hydrophobic solvent systems, resulting in articles of manufacture having a coating made from a water-reactive isocyanate-containing polymer that also incorporates a water-soluble oligodynamic metal salt.

In one variation, a device (e.g., a silicone catheter) can be coated with a lubricious coating incorporating an oligodynamic metal to a final surface concentration of at least about 5 $\mu g/cm^2$ even when the coating is compounded in a highly hydrophobic solvent. The oligodynamic metal may be a water-soluble metal salt. For example a silicone catheter may be coated with a combination of a reactive primer and a reactive top coat. Silver salts can be added to both the primer and the top coat, and may result in a concentration of silver that can be continuously released from the coated device, particularly when it is immersed in water or biological fluids.

In general, a coating solution comprising an highly hydrophobic solvent system (e.g., for compounding a coating containing water-reactive functional groups, such as isocyanates) can be formulated to include oligodynamic metal salts to produce coatings having different concentrations of oligodynamic metal salts (e.g., greater than 5 $\mu g/cm^2$, greater than 10 $\mu g/cm^2$, greater than 20 $\mu g/cm^2$, etc.) by controlling the formulation method and the amount of water added to the coating solution. For example, the amount of water added to the coating solution can be adjusted to between about 100-10,000 ppm, such as between 100 and 1,000 ppm. In some variations, the amount of water is adjusted to between about 200-500 ppm. The amount of water may be adjusted by any appropriate method, including titration and addition (or removal) of water. The amount of water absorbed into hydrophobic coating solutions may also be increased by adding hygroscopic compounds (e.g., compounds that incorporate water and may "absorb" water from their surroundings), such as PEO and other hydrophilic polymers. The amount of water in the hydrophobic coating solution may be adjusted by agitating the solution for an appropriate hydration time. For example, hygroscopic compounds and/or water may be added to the coating solution, and the solution may be continuously agitated (e.g., stirred) for greater than 24 hours to adjust the water concentration in the solution. Thereafter, one or more oligodynamic metals (e.g., oligodynamic metal salts) can be added.

The amount of oligodynamic metal salt dissolved into the coating solution is a function of many variables. The amount of water in the solution, the amount and type of oligodynamic metal salts added, the time and method of agitation and the temperature of the solution can all influence the amount of salt dissolved into the coating solution. Higher concentrations of salts can be introduced, for example, by using more water, longer agitation times and more rigorous agitation.

The amount of oligodynamic metal salt added to the coating solution can also be used to control the amount of salt in the final coating. The salt is typically added in excess, and after a period of agitation, the excess is filtered from solution. The greater the amount of oligodynamic metal salt added to the coating solution the greater and the faster the salt will be absorbed.

After the desired agitation period, the excess oligodynamic metal salt is filtered from the coating. Another factor influencing the amount of salt in the final coating is the porosity of the filter used. The more coarse the filter, the higher the amount of oligodynamic metal salt in the coating. This suggests that in addition to the oligodynamic metal salt which has dissolved in the coating solution there is also some fine suspended salt whose particle size is determined by the porosity of the filter.

The coating solution may be used to produce a coating directly on a substrate, or the substrate may be coated with an initial primer coating designed to improve the adhesion of the coating to the substrate. The coating is generally, but not always, hydrophilic, such that it becomes lubricious by absorbing water when in contact with aqueous media, such as body fluids. The coating solution frequently comprises isocyanate groups (including polymer/monomers having reactive isocyanate groups) which polymerize to form polymethanes once the coating has dried. Examples of coating formulations that use isocyanates and may be used in coating solutions of the invention can be found, for example, in U.S. Pat. Nos. 5,077,352; 5,160,790; 5,179,174; 5,290,585; and 6,329,488, the disclosures of which are all incorporated by reference herein. Thus, the coating solution may form a polyurethane coating with associated oligodynamic metals and/ additional components such as hydrophilic polymers like PRO and PVP. In some variations, the coating solution comprises a polyisocyanate, a polyol and PEO, compounded in a hydrophobic solvent (e.g., methylene chloride) and a small amount of water, to which at least one water-soluble oligodynamic metal salt (e.g., silver) is added as described herein.

Oligodynamic metals include, but are not limited to, silver, gold, zinc, copper, platinum, cerium, gallium, osmium, mercury, and the like. Oligodynamic metals may include salts, colloids, ions or metals. The salts may be different salts of the same oligodynamic metal or may be salts of different oligodynamic metals. Salts of oligodynamic metals may contain anions that include, but are not limited to, acetates, ascorbates, benzoates, bitartrates, bromides, carbonates, chlorides, citrates, folates, gluconates, iodates, iodides, lactates, laurates, oxalates, palmitates, perborates, phenosulfonates, phosphates, propionates, salicylates, stearates, succinates, sulfadiazines, sulfates, sulfides, sulfonates, tartrates, thiocyanates, thioglycolates, thiosulfates, and the like. The salts may also comprise oxides, including, but not limited to, oxides of oligodynamic metals such as silver, gold, zinc, copper, and the like.

As described above, a coating is typically compounded in an initially anhydrous and/or highly hydrophobic solvent or solvent system. When the coating solution includes an isocyanate, the solvent used does not, according to various embodiments, react with the isocyanate, and may protect the isocyanate from reacting with water by its hydrophobic nature, because the solvent does not absorb appreciable amounts of water from the air the coating operation. Examples of such anhydrous and/or highly hydrophobic solvents include but are not limited to solvents including methylene choloride, methylene bromide, dichloroethane, chloroform, hexane, cyclohexane, benzene and toluene. These hydrophobic solvents are generally immiscible with water, and are usually nonsolvents for the oligodynamic metal salts of interest.

However, many hydrophilic and hygroscopic monomers and polymers that contain isocyanate-reactive functional groups, such as hydroxyl groups, are soluble in anhydrous and/or highly hydrophobic solvents or solvent systems. The ability of these hydrophilic components to hydrogen bond with water is believed to be important to the dissolution of water into the hydrophobic solvent system and to the ultimate dissolution of the water-soluble oligodynamic metal salt into the coating solution. For example, the coating may include a hydrophilic polymer such as polyethylene oxide (PEO) that is hygroscopic and can hydrogen bond with water to aid the absorption of water and the dissolution of oligodynamic metal salts into the hydrophobic solvent system. The coating may also a include polyol, which is both hygroscopic and has abundant hydroxyl functional groups that ale reactive with isocyanates to polymerize polyurethane for the coating matrix. Examples of other hydrophilic polymers and compounds that may be used in the coatings of the invention include, but are not limited to, polyethylene glycol (PEG), polysaccharides, hyaluronic acid and its salts and derivatives, sodium alginate, chondroitin sulfate, celluloses, chitin, chitosan, agarose, xanthans, dermatan sulfate, keratin sulfate, emulsan, gellan, curdlan, amylose, catrageenans, amylopectin, dextrans, glycogen, starch, heparin sulfate, limit dextrins and fragments thereof; synthetic hydrophilic polymers, poly (vinyl alcohol), and poly(N-vinyl)pyrrolidone (PVP).

As an example, when methylene chloride, a highly hydrophobic solvent, is used to form a coating solution, the amount of water in the solution may be controlled so that it is between about 100 ppm and about 1000 ppm. In particular, the amount of water may be adjusted between about 200 ppm and about 500 ppm. Methylene chloride is generally observed to only absorb a very small amount of water from the air (e.g., typically less than 50-100 ppm). Higher amounts of water in methylene chloride are difficult to achieve without additional manipulation. It has been found that the dissolution of hygroscopic materials into the methylene chloride significantly increases the amount of water absorbed into the coating solution. For example, a hygroscopic material can increase the amount of water in this example by another 100 to 900 ppm or more, depending upon the concentration added, the amount of water added and the treatment of the solution.

Without being limited by theory, the inventor has hypothesized that small amounts of water within the highly hydrophobic solvent system may dissolve water-soluble oligodynamic metals, such as silver salts, and that this process is enhanced by inclusion of hydrophilic compounds such as water-soluble polymers, in the coating solution. Further, the amount of water in such solutions can be increased by the time and degree of agitation of the solution, as described further below. Thus, the amount of water included in the highly hydrophobic solvent system can be increased to between about 100 to 10,000 ppm, depending on the solvent system. In some variations, the amount of water may be between about 100 and about 1000 ppm. In some variations, the amount of water maybe between about 200 and about 500 ppm.

The amount of both water and oligodynamic metal salt included in the hydrophobic solvent coating solution may be increased by both the time and degree of agitation of the coating solution. For example, the solution may be stirred, shaken, sonicated, dispersated, etc. The solution may be agitated for any appropriate amount of time. In general, the longer the solution is agitated, the more water (in ppm), and thus the more water-soluble oligodynamic metal salt, may be included. For example, the solution may be agitated for as little as 1 hour, to as much as several days or weeks. Water may be added to adjust the final amount of water to any appropriate approximate level within the limits of water solubility in the solution. As described in the example where methylene chloride is the primary solvent, the amount of water in the solution may be adjusted to between about 100 and 1000 ppm, such as between about 200 to 500 ppm.

The amount of water in the system will vary depending on the solvents used, the hydrophilic components in the coating, the sensitivity of the coating monomers/polymers to water, etc. Less hydrophobic solvents can be used to allow inclusion of mole water, but their use must be balanced with the sensitivity of the reactive components of the coating, such that the coating chemistry produces good quality coatings from these solvent systems.

According to one aspect of the invention, a polyol is added to the coating solution to react with a polyisocyanate to form a polyurethane coating upon drying. Examples of polyols which could be used in this embodiment include, but ate not limited to polyester polyols, polyether polyols, modified polyether polyols, polyester ether polyols, caster oil polyols, polyacrylate polyols, and the like. Useful polyols may be soluble in the anhydrous or hydrophobic solvents.

Any appropriate amount of oligodynamic metal may be added to the coating formulation. The oligodynamic metal may be added before or after the addition of the hygroscopic material, any polyol, any other components, any additional water, and agitation of the formulation. In a preferred embodiment, the oligodynamic metal salt is added after a solution is prepared which contains a hygroscopic polymer, a polyol and additional water. For example, the amount of oligodynamic metal may be added as a percent of the amount of other solids (e.g., coating solids) in the solution. In some variations, the oligodynamic metals (e.g. salts) may be added so that they constitute between about 10 and about 50 percent of the weight of the polymer solids in the coating. In some variations, oligodynamic metals (e.g., salts) may be added so that they are between about 15 and about 30 percent of the weight of the polymer solids in the coating. In some variations, oligodynamic metal salt is added so that the amount is greater than about 50 percent of the weight of the polymer solids in the coating.

After the addition of the oligodynamic metal material (e.g., salts), the solution may be agitated in any appropriate manner for any appropriate amount of time in order to put as much of the oligodynamic metal into solution as is possible, i.e. to reach the saturation point of the salt within the coating solution. As described above, the solution may be agitated by stirring, shaking, sonicating, dispersion with a dispersator, etc. In some variations, the solution (including the oligodynamic metal salt) is agitated for shorter periods of time such as one to several hours. In other variations, the coating solution is agitated for several days or even several weeks. In an embodiment described above, the coating solution with oligodynamic metal salt is stirred for three days before the excess salt is removed by filtration.

Once the coating solution has been formulated (e.g., including the hydrophilic components and added water) and agitated with the added oligodynamic metal salt for the desired period, the coating solution may be filtered. The oligodynamic metal salts are generally added in excess to the amount that can dissolve into the coating solution to encourage saturation of the solution with the salt. The excess salt must then be filtered to particulate matter in the coating that could be of the size to cause patient discomfort in a coated medical device. Any appropriate filter or filtration system that is compatible with the coating solution may be used In some variations, the filter comprises a size filter such as a 50 micron filter, a 100 micron filter, a 150 micron filter, etc.

After filtering, the coating solution may be used to coat an appropriate substrate, or additional coating components may be added before coating begins. In some examples where the water-reactive component of the coating is adversely affected by the water in the system, for example, when long agitation times are needed to achieve the desired oligodynamic metal salt levels in a coating, the water sensitive component can be added after filtration and just before coating the substrate. In this way, the time of exposure of the water-reactive component to the water in the coating solution can be limited. As an example, in the coating solution comprising a polyisocyanate, a polyol and PEO in methylene chloride, it has been found that addition of the polyisocyanate after the addition of water and oligodynamic metal salt produces a more durable coating. In this example, the coating solution with all the components except the polyisocyanate is stirred for three days and then filtered. After filtration, the polyisocyanate is added, mixed for one hour; and then coated onto a medical device.

A coating may be applied to the substrate by any appropriate method. The substrate may be dipped, sprayed, painted, ox otherwise coated with the coating solution and then dried. As an example, when the substrate is a catheter (e.g., a silicone catheter), it can be dipped into the coating solution at a rate of about 15-80 inches per minute (ipm), for example about 40 ipm. The catheter can be allowed to remain or dwell in the coating solution for some amount of time (e.g., for 0-30 seconds) or it can be immediately removed. In this example, the catheter may be removed at a late of about 10-80 ipm, preferably about 15 ipm. Once the catheter has been coated with the coating of the invention, it can be allowed to air dry (e.g., for more than 15 minutes, 1 hour, etc.). The catheter may then be dried with a hot air stream or in an oven at a temperature of approximately 45 to 100° C. for about 5-60 minutes (e.g., 30 min) to remove residual solvent.

The coating solutions may also contain additional materials, including additional antimicrobial materials. For example, the compositions containing silver salts may also contain salts of other metals that enhance the antimicrobial effect of the silver, such as the platinum group metals, or other metals that promote galvanic action. Additional medicinal compounds may also be included. For example, antimicrobials, antibiotics, antifungal agents, anesthetics, anti-inflammatory agents, analgesics, anticancer agents, antiviral agents, antithrombogenic agents, anesthetics, anti-inflammatory agents, analgesics, anticancer agents, vasodilatation substances, wound healing agents, angiogenic agents, angiostatic agents, immune boosting agents, growth factors and other biological agents, and the like.

Examples of methods for making a coating solution of the invention, coating a substrate with the coating solution, and articles coated with the coatings are described below.

EXAMPLE 1

Silver Nitrate Coating Solution

A coating solution was prepared containing silver nitrate in a solution of polyethylene oxide (PEO), a polyisocyanate, a polyol and water in methylene chloride using the method below. First, a 1.08% solution of PEO (Polyox N750, Dow Chemical) was prepared by adding 5.5 g PEO, 1.761 g of polyol (P12, Caschem Chemical) and 0.15 g of deionized water (300 ppm based on solution weight) to 500 g methylene chloride, and stirring over night to dissolve the PEO. Then, 3.52 g of silver nitrate (29% based on weight of solids in the coating) was added to the coating solution and stirring was continued for 3 days. The solution was then filtered thru a 100 micron bag filter to remove the excess undissolved silver nitrate. Next, 1.349 g of polyisocyanate (Desmodur L67 MPA/X, Bayer Chemical) was added to the solution, and stirring was continued for one hour.

EXAMPLE 2

Coated Silicone Foley Catheters

Before coating with the silver nitrate coating solution from Example 1, silicone Foley catheters were first primed with a silicone-polyurethane copolymer (preparation described in U.S. Pat. No. 6,329,488) and dried in an oven at 60° C. for 15 minutes. The primed catheters were then coated with coating solution from Example 1 by dipping the catheters in the coating solution with an in speed of 40 ipm, no dwell in solution and an out speed of 15 ipm. The catheters were then allowed to dry in air for about 15 minutes and were finally dried in an oven at 60° C. for 30 minutes. The resulting coated catheters had silver concentration of 16.46 $\mu g/cm^2$.

EXAMPLE 3

Silver Acetate Coating Solution

Prophetic Example: A coating solution can be prepared as in Example 1 above, except that instead of adding 3.52 g of silver nitrate to the coating solution, 1.52 g of silver acetate (15% based on weight of solids in the coating) can be added to the coating solution.

EXAMPLE 4

Coating Solution With Isocyanate Added Last

A coating solution was prepared as in Example 1, except that the 1.349 g of polyisocyanate (Desmodur L67 MPA/X, Bayer Chemical) was added with the polyol.

While the invention has been described in terms of particular variations and illustrative figures, those of skill in the art will recognize that the invention is not limited to the variations or figures described. In addition, where methods and steps described above indicate certain events occurring in certain order, those of skill in the art will recognize that the ordering of certain steps may be modified and that such modifications are in accordance with the variations of the invention. Additionally, certain steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method for coating a substrate comprising:
    combining at least one polyol and at least one hydrophilic polymer in at least one hydrophobic solvent to yield a coating composition;
    adjusting the water in the coating composition to between about 100 to about 1000 ppm;
    combining a water-soluble oligodynamic metal salt with the coating composition;
    filtering excess oligodynamic metal salt that is not dissolved or absorbed into the coating from the coating composition;
    combining a polyisocyanate with the coating composition; and
    coating a substrate with the coating composition.

2. The method of claim 1, wherein the step of coating a substrate comprises coating a primed silicone substrate.

3. The method of claim 1, wherein the step of coating a substrate comprises coating a catheter.

4. The method of claim 1, wherein the coating composition is prepared in a hydrophobic solvent comprising at least one of methylene chloride, methylene bromide, ethylene dichloride, and chloroform.

5. The method according to claim 1, wherein the steps are performed in any order sufficient for coating a substrate.

6. The method of claim 1, wherein the polyisocyanate is combined with the at least one polyol and at least one hydrophilic polymer in at least one hydrophobic solvent to yield a coating composition.

7. The method of claim 1, wherein the step of adjusting the water in the coating solution further comprises adding water to the coating solution and agitating the solution.

8. The method of claim 7, wherein the step of agitating the coating solution comprises stirring the coating solution for at least 24 hours.

9. The method of claim 1, wherein the step of adding a water-soluble oligodynamic metal salt further comprises agitating the coating solution for at least 24 hours.

10. The method of claim 1, wherein the substrate is coated with a primer before coating with the coating solution.

* * * * *